United States Patent
Quan et al.

(10) Patent No.: US 11,484,695 B2
(45) Date of Patent: Nov. 1, 2022

(54) MICRONEEDLE PATCH CASE (71) Applicant: COSMED PHARMACEUTICAL CO., LTD., Kyoto (JP)

(72) Inventors: Ying-shu Quan, Kyoto (JP); Kiyotsune Higuchi, Kyoto (JP); Fumio Kamiyama, Kyoto (JP)

(73) Assignee: COSMED PHARMACEUTICAL CO., LTD., Kyoto (JP)

( * ) Notice: Subject to any disclaimer, the term of this patent is extended or adjusted under 35 U.S.C. 154(b) by 895 days.

(21) Appl. No.: 16/084,923

(22) PCT Filed: Mar. 16, 2017

(86) PCT No.: PCT/JP2017/010639
§ 371 (c)(1),
(2) Date: Sep. 13, 2018

(87) PCT Pub. No.: WO2017/159779
PCT Pub. Date: Sep. 21, 2017

(65) Prior Publication Data
US 2019/0099590 A1  Apr. 4, 2019

(30) Foreign Application Priority Data
Mar. 16, 2016  (JP) .............................. JP2016-074692

(51) Int. Cl.
*A61J 1/14* (2006.01)
*A61M 37/00* (2006.01)
*A61J 1/00* (2006.01)

(52) U.S. Cl.
CPC ............ *A61M 37/0015* (2013.01); *A61J 1/00* (2013.01); *A61J 1/14* (2013.01); *A61M 37/00* (2013.01); *A61M 2037/0061* (2013.01)

(58) Field of Classification Search
CPC .............. A61M 37/0015; A61M 37/00; A61M 2037/0061; A61M 2037/0023;
(Continued)

(56) References Cited

U.S. PATENT DOCUMENTS

| 2002/0087182 A1 | 7/2002 | Trautman et al. |
| 2002/0091357 A1 | 7/2002 | Trautman et al. |

(Continued)

FOREIGN PATENT DOCUMENTS

| CN | 1901840 A | 1/2007 |
| CN | 101076367 A | 11/2007 |

(Continued)

OTHER PUBLICATIONS

Korean Office Action for the Application No. 10-2018-7026472 dated Jun. 21, 2021.

(Continued)

*Primary Examiner* — Bhisma Mehta
*Assistant Examiner* — William R Frehe
(74) *Attorney, Agent, or Firm* — Cheng Law Group, PLLC (57) ABSTRACT

Providing a patch case that is easily attached to a microneedle applicator, easily separable from the microneedle patch upon insertion and disposable for use. The main feature of the patch case according to the present invention is characterized in that it is made of a thermoplastic polymer and is capable of holding a microneedle patch comprising a support film which can be heat-sealed with the thermoplastic polymer.
Preferably, the thermoplastic polymer of the body and the fusible material of the support film are both polyolefins or both are the same thermoplastic polymer. In addition, if the patch case is attached to the front of the applicator, sanitary (Continued)

situation can be maintained even with continuous use of the applicator, since the applicator does not contact the skin of the recipient.

6 Claims, 5 Drawing Sheets

(58) Field of Classification Search
CPC .... A61M 2037/003; A61M 2037/0038; A61M 2037/0046; A61M 2037/0053; A61K 9/0021

See application file for complete search history.

(56) References Cited

U.S. PATENT DOCUMENTS

| | | | |
|---|---|---|---|
| 2002/0123675 A1 | 9/2002 | Trautman et al. | |
| 2005/0096586 A1 | 5/2005 | Trautman et al. | |
| 2005/0148926 A1 | 7/2005 | Trautman et al. | |
| 2005/0228340 A1* | 10/2005 | Cleary | A61B 17/205 604/46 |
| 2006/0095061 A1 | 5/2006 | Trautman et al. | |
| 2006/0142691 A1 | 6/2006 | Trautman et al. | |
| 2007/0027427 A1 | 2/2007 | Trautman et al. | |
| 2007/0255251 A1 | 11/2007 | Panchula et al. | |
| 2007/0299388 A1* | 12/2007 | Chan | A61K 9/0021 604/46 |
| 2008/0108958 A1 | 5/2008 | Carter et al. | |
| 2009/0234301 A1* | 9/2009 | Tomono | A61M 37/0015 604/272 |
| 2010/0196367 A1 | 8/2010 | Day | |
| 2010/0256568 A1 | 10/2010 | Frederickson et al. | |
| 2010/0261176 A1 | 10/2010 | Mitragotri et al. | |
| 2011/0212485 A1 | 9/2011 | Mitragotri et al. | |
| 2011/0295149 A1 | 12/2011 | Mitragotri et al. | |
| 2012/0004592 A1 | 1/2012 | Mitragotri et al. | |
| 2012/0184916 A1* | 7/2012 | Kobayashi | A61M 37/0015 604/272 |
| 2012/0253238 A1 | 10/2012 | Mitragotri et al. | |
| 2014/0107560 A1 | 4/2014 | Mitragotri et al. | |
| 2014/0336487 A1* | 11/2014 | Wang | G01N 33/48785 600/352 |
| 2014/0339117 A1* | 11/2014 | Quan | A61M 37/0015 206/438 |
| 2014/0364801 A1 | 12/2014 | Trautman et al. | |
| 2015/0209505 A1 | 7/2015 | Hanson et al. | |
| 2015/0217045 A1 | 8/2015 | Bente, IV et al. | |
| 2015/0275174 A1 | 10/2015 | Mitragotri et al. | |
| 2015/0290444 A1* | 10/2015 | Wirtanen | A61M 37/0015 604/46 |
| 2015/0297827 A1 | 10/2015 | Hanson et al. | |
| 2015/0344834 A1 | 12/2015 | Mitragotri et al. | |
| 2016/0074644 A1 | 3/2016 | Cao et al. | |
| 2016/0121092 A1* | 5/2016 | Kato | A61M 37/0015 604/173 |
| 2016/0235392 A1 | 8/2016 | Mitragotri et al. | |
| 2016/0325081 A1* | 11/2016 | Kato | A61M 37/0015 |
| 2017/0105673 A1 | 4/2017 | Mitragotri et al. | |
| 2017/0266428 A1 | 9/2017 | Frederickson | |
| 2017/0274196 A1* | 9/2017 | Nordon | B81B 1/006 |
| 2018/0243502 A1 | 8/2018 | Hanson et al. | |
| 2018/0304006 A1 | 10/2018 | Bente, IV et al. | |
| 2019/0083769 A1* | 3/2019 | Nagai | A61M 37/0015 |
| 2019/0240470 A1* | 8/2019 | Frederickson | A61M 37/0015 |
| 2021/0024351 A1* | 1/2021 | Rajaram | C12M 23/12 |
| 2021/0330951 A1* | 10/2021 | Kim | A61L 31/04 |
| 2021/0330952 A1* | 10/2021 | Kim | G01N 33/49 |

FOREIGN PATENT DOCUMENTS

| | | |
|---|---|---|
| CN | 101208129 A | 6/2008 |
| CN | 101254326 A | 9/2008 |
| CN | 102395881 A | 3/2012 |
| CN | 103263727 A | 8/2013 |
| CN | 203436688 U | 2/2014 |
| CN | 104640584 A | 5/2015 |
| JP | 2004-510530 A | 4/2004 |
| JP | 2004-510534 A | 4/2004 |
| JP | 2007-509706 A | 4/2007 |
| JP | 2007-535346 A | 12/2007 |
| JP | 2008-534152 A | 8/2008 |
| JP | 2008-543528 A | 12/2008 |
| JP | 2009-529400 A | 8/2009 |
| JP | 2012-213586 A | 11/2012 |
| JP | 2013-226427 A | 11/2013 |
| JP | 2013-252869 A | 12/2013 |
| JP | 2014-42788 A | 3/2014 |
| JP | 2014-79622 A | 5/2014 |
| JP | 2016-30072 A | 3/2016 |
| WO | WO-2005/094526 A2 | 10/2005 |
| WO | WO-2014/187338 A1 | 11/2014 |
| WO | WO-2015/005143 A1 | 1/2015 |
| WO | WO-2015/111673 A1 | 7/2015 |

OTHER PUBLICATIONS

International Search Report for the Application No. PCT/JP2017/010639 dated Jun. 13, 2017.

Written Opinion of the International Searching Authority (PCT/ISA/237) for Application No. PCT/JP2017/010639 dated Jun. 13, 2017.

The First Office Action for the Application No. 201780023450.4 from The State Intellectual Property Office of the People's Republic of China dated Jun. 9, 2020.

The Second Office Action for the Application No. 201780023450.4 from The State Intellectual Property Office of the People's Republic of China dated Jan. 19, 2021.

Australian Examination Report No. 1 for the Application No. 2017232609 dated Mar. 3, 2021.

Supplementary European Search Report for the Application No. 17 766 775.5 dated Oct. 11, 2019.

Australian Examination Report No. 2 for the Application No. 2017232609 dated Aug. 2, 2021.

The Third Office Action for the Application No. 201780023450.4 from The State Intellectual Property Office of the People's Republic of China dated Aug. 9, 2021.

* cited by examiner

MICRONEEDLE PATCH CASE

TECHNICAL FIELD

The present invention relates to a patch case for convenient for preservation, delivery and application of microneedle patches.

THE BACKGROUND OF THE INVENTION

Oral and transdermal administration are commonly used to apply drugs into the human body.

Injection is a typical percutaneous route of application, but is a cumbersome, painful and unwelcome technique with possible infection.

In transdermal administration, the stratum corneum acts as a barrier to drug transparent, and simply applying the drug to the skin surface is not necessarily sufficient for permeability.

On the other hand, by piercing the stratum corneum using a minute needle, that is, a microneedle, the drug permeation efficiency can be remarkably improved.

A microneedle array is obtained by integrating a large number of microneedles on a board.

The microneedle patch is a product that is easily used by adding an adhesive sheet of microneedle array supporting the microneedle array when it is applied to the skin, a protection release sheet for protecting the adhesive sheet for storage.

It is desirable that the microneedle patches be stored safely and hygienically, before delivered to the user. The patches should be packaged for safety and easy use until used.

For this purpose, it is convenient to store, transport, and retain the patch in a convenient patch case.

When the microneedle array is administered to the skin, the applicator is often used as a puncture auxiliary, because the skin is generally soft and it is not easy to puncture the microneedles simply by pressing with the fingers.

If the patch case can be attached to and inserted into the applicator, it is unnecessary for the user to touch the microneedle array by hand, which is not only hygienic but also convenient for the user.

That is, the patch case in this invention is a container for storing, transporting, and holding a microneedle patch, and is a container that can be attached to an applicator while holding a microneedle patch, and can apply the microneedles to a subject.

Several containers for storing micro-needle patches have been reported (Patent Documents 1 and 2).

However, there are not many reports of patch cases in which a microneedle patch is attached to an applicator while being housed.

In a cylindrical patch holder (equivalent to a patch case) that can be attached to the applicator body, the microneedle patch is attached to a shoulder (step) for mounting the central of the patch holder (Patent Documents 3 and 4).

When the patch holder is attached to the applicator and impacted by the applicator, the frangible attachment area of the microneedle patch is ruptured and separated, and the microneedle patch leaves the patch holder and penetrates the skin surface.

The patch holder may also be disposable.

Similar patch retainers are disclosed in other documents (Patent Documents 5, 6, 7).

In a microneedle array cartridge (equivalent to a patch case) comprising a material web (board) and a container (cover), the microneedle array is attached to an applicator as a cartridge (Patent Document 8).

A patch holder (equivalent to a patch case) inserted from the side of the applicator has a mounting shoulder and can hold a microneedle patch on a weakly tacky underside (U.S. Pat. No. 9).

PRIOR ART REFERENCES

Patent Document

Patent Document 1 JP-A-2012-213586
Patent Document 2 JP-A-2014-079622
Patent Document 3 JP-A-2004-510534 (Japanese Patent No. 4104975)
Patent Document 4 JP-A-2009-529400
Patent Document 5: JP-A-2004-510530 (Japanese Patent No. 4198985)
Patent Document 6 JP-A-2007-509706 (Japanese Patent No. 4682144)
Patent Document 7 JP-A-2008-534152
Patent Document 8 JP-A-2008-543528
Patent Document 9 JP-A-2014-042788

SUMMARY OF THE INVENTION

Problems to be Solved by the Invention

The issue to be solved by the present invention is to provide a patch case which is easy to use to a microneedle applicator, easily separable from the microneedle patch when necessary, and disposable.

Means for Solving the Problem

In order to solve the above issues, a body of a patch case according to the present invention is made of a thermoplastic polymer, and a support film of an adhesive tape of a microneedle patch is made of a material that can be thermally fused with the patch case and can hold the microneedle patch.

In order to adhere the microneedle patch to the patch case, there are a method of attaching the microneedle patch to a bottom portion of an edge portion of the patch case and a method of attaching the microneedle patch to a top of the edge portion of the patch case. Regarding the attaching, there are a method of heat fusion bonding and a method of bonding with a pressure-sensitive adhesive.

In the present invention, the term "bottom" in the patch case means the one closer to the skin at the time of use, and the term "top" means the one closer to the applicator at the time of use.

Applying the adhesive to the edge of the patch case beforehand increases the number of processes and increases the cost.

However, when adhesively attached to the top of the edge, the adhesive layer of the microneedle patch can be utilized, so there is no additional process.

However, when attached to the top of the edge, it many does not peel off well when impacted by the applicator, which is of practical difficulty.

Such difficulties do not arise if a thermal fusion process is used to attach to the bottom of the edge.

The thermal fusion of the support film of microneedle patch with the patch case does not require a special method. The tip of the sharp metal rod may be heated to a temperature equal to or higher than the melting point of the thermoplastic polymer and pressed against the thermal fusion part.

The thermal fusion surface fuses the support film to the bottom of the patch case.

In this case, a sharp metal rod is pressed from the surface of the support film to which the adhesive is applied to thermally fuse the film and the case.

In order to remove the metal bar after fusing, it is necessary to make the fusion strength between the patch case and the microneedle film stronger than the adhesion strength between the metal bar and the adhesive surface.

For this purpose, if the coating thickness of the pressure-sensitive adhesive is too thick, the bonding strength with the metal rod becomes too strong, and therefore the thickness of the pressure-sensitive adhesive layer needs to be 300 μm or less.

In order to perform fusing to the melting point or higher of the thermoplastic polymer, any of heat fusing, heat fusing by high frequency, heat fusing by laser, and the like may be used.

In order to easy the heat fusion bonding, it is desirable that the material of the support film is a thermoplastic polymer film or a nonwoven fabric.

When the support film is a laminate film of a multiple of films, if the back side is a thermoplastic polymer film, the front side may be any film as long as it can be used as an adhesive sheet by applying an adhesive.

In this statement, when a microneedle array is adhered and fixed to a support film, this side of the support film is defined as the surface of the support film and the opposite surface is defined as the back surface.

In the present invention, the periphery portion of the back surface of the support is heat-sealed to the patch case.

The material of the patch case is not particularly limited as long as it is a thermoplastic resin which is solid at room temperature, and polyolefin resin, polyvinyl chloride, polycarbonate, nylon resin, polyethylene terephthalate (PET) or the like can be used. Polyolefin resin is preferable because it is easy to mold a material at low heating molding temperature.

Specifically, polyethylene, polypropylene, ethylene-propylene copolymer, ethylene-vinylaetate copolymer, and the like are suitable.

The support film may be a thermoplastic resin or a nonwoven fabric, but the same material as that of the support film and that of the patch case is desirable because it is easy to fuse the same type of resin for thermal fusion.

As the support film, specifically, polyolefin resin, polyvinyl chloride, polycarbonate, nylon resin, polyethylene terephthalate (PET), or the like can be used.

The microneedle patch, which is heat-sealed and integrated with the patch case, is set on the applicator together with the case.

Although there is no limitation the applicator itself, striking by releasing the energy compressed by the spring is suitable.

When the applicator described in Patent Document 9 is used, a piston is used to perform a high-speed impact, and the thermal fusion is peeled off to administer the microneedle patch together with the support film to the skin.

In the present invention, a spring having a spring constant of 0.258 N and a length of 70 mm was used.

It is important to fuse the back surface of the support film having the microneedle array between the patch case and the surface adhesive layer with necessary and sufficient strength.

If the thermal fusion is too strong, a patch case in which the support film is thermally fused is attached to an applicator, and a portion that does not peel off is apt to occur when the support film with microneedles is peeled off from the patch case by a high-speed impact of a piston.

This results in the phenomenon that when the microneedle array is administered to the skin, the microneedles are not administered in parallel to the skin, but a portion is administered to the skin and the remainder is subsequently administered.

Such a phenomenon is confirmed by the fact that the needle is partially bent in one direction when the microneedle array after skin application is collected and observed under a microscope.

Observation of the skin at the applied site more accurately makes clear the administration status of the needle.

If the thermal fusion is too weak, the adhesive surface tends to adhere to the metal rod during the thermal fusion process. In addition, the support film may detach from the case during storage, move, attachment to an applicator, and the like, which is not suitable.

The present inventors have conducted various studies on the dermal fusion between the support film and the patch case.

Figure 3:
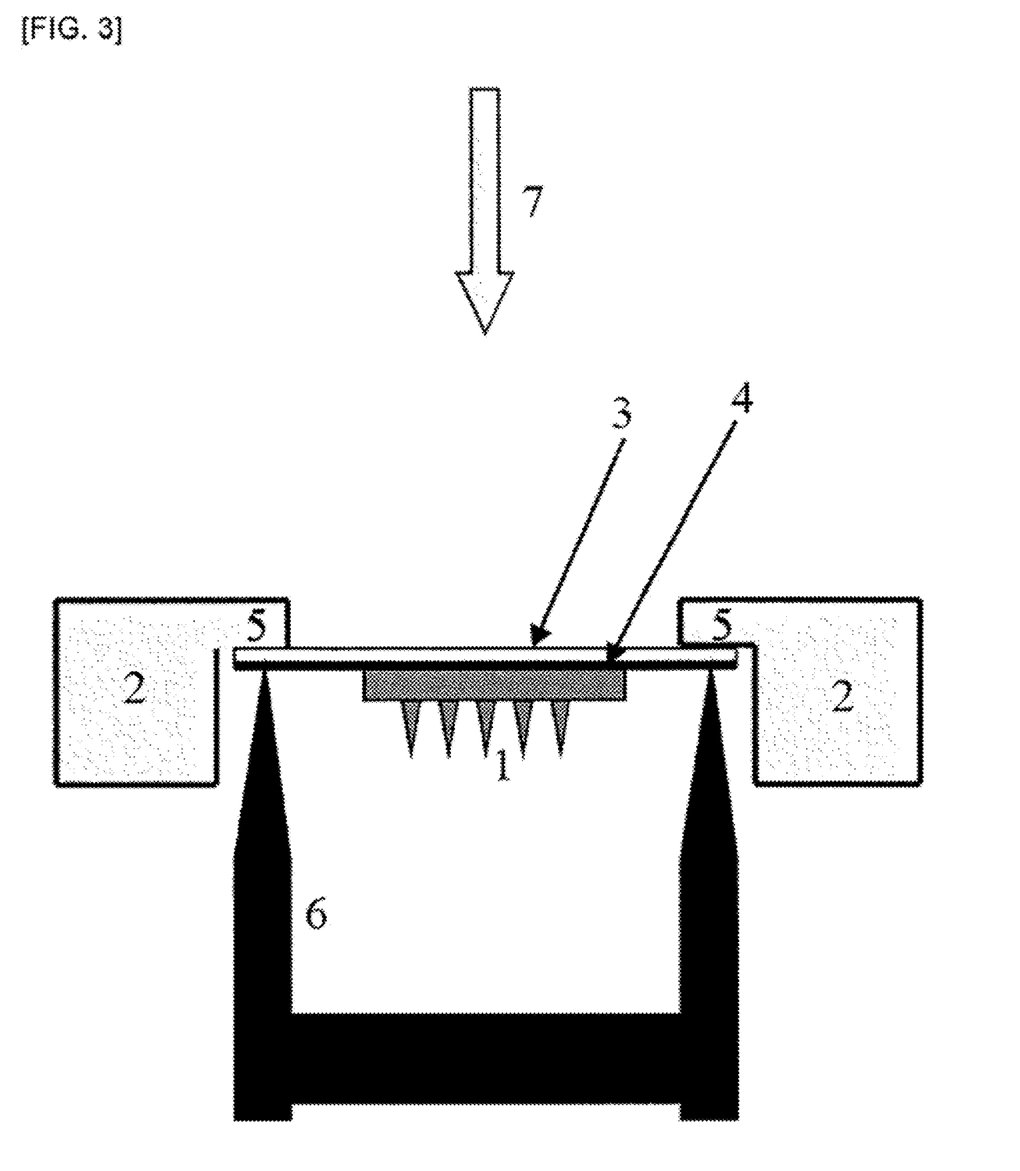
FIG. 3 is an explanatory view of attachment of a microneedle patch to a patch case by thermal fusion.

An arrangement diagram of the patch case, the support film, and the microneedle array is shown in FIG. 3.

A support film with a microneedle array is administered to the skin (lower surface) by the impact of the piston from the top of the figure.

The pattern of the heat fusion is not particularly limited.

It may be a point fusion, a dash line fusion, or a continuous line fusion.

In the case of point fusion, two-point fusion tends to become unstable, and therefore, a multiple of fusions (3 to 12-point fusion or 3 to 6-point fusion) of three-point fusion or more are desirable.

Figure 7:
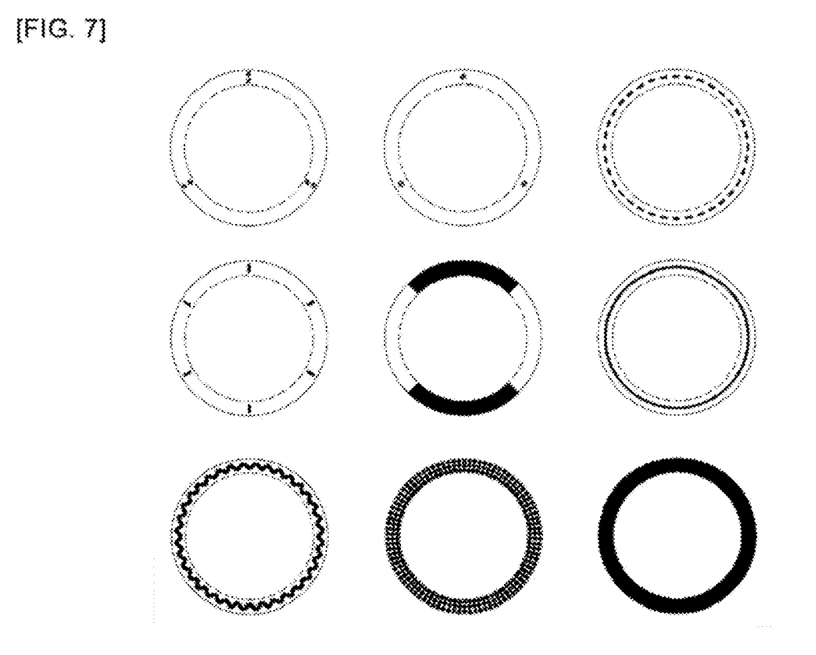
FIG. 7 shows various heat fusion patterns of the patch case and the support film. Upper left: 3-point fusion (2 points in one location), middle left: 6-point fusion (oval), lower left: wavy solid line fusion, middle upper: 3-point fusion (perfect circle), middle: solid line partial fusion, middle: full point fusion, upper right: dash line fusion, middle right: solid line fusion, lower right: full point fusion.

Various fusing patterns are possible, an example of which is shown in FIG. 7.

The strength of the thermal fusion was quantified by compressing a 1 cm diameter cylindrical rod from above a patch case with a support film having the configuration shown in FIG. 3 using a tensile tester.

In the present invention, the strength at which a cylindrical rod having a diameter of 1 cm is pressed from the upper surface of the support film to break the heat fusion is defined as the "breaking strength".

Experimentally, the breaking strength is determined from the values of the stress at compression of the welded support film to the yield stress of the strain curve.

Figure 8:
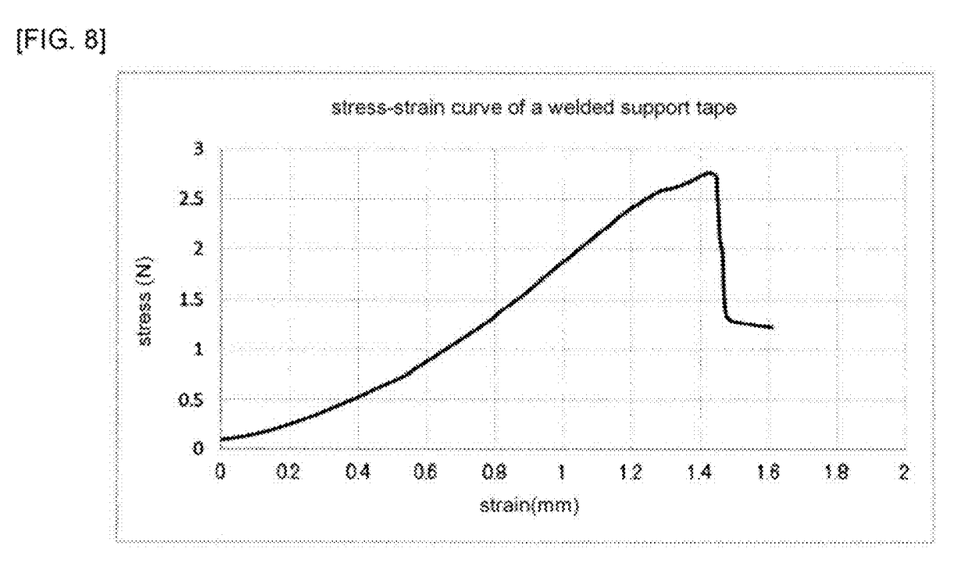
FIG. 8 is a stress-strain curve of a welded support film.

FIG. 8 shows an example. The horizontal axis represents strain (mm) and the vertical axis represents stress (N), and a yield point is observed at 1.4 mm strain, and the value is 2.9.

Various samples having different thermal fusing conditions and different fusing patterns were prepared, and the samples whose break strength was measured were set in an applicator and microneedles were administered to the skin to observe the results.

As a result, if the breaking strength was too strong, it became difficult to uniformly apply the microneedles to the skin.

In addition, if it was too weak, a drawback such as a part of the heat-bonded portion peeled off during handling was observed.

From these results, the breaking strength is preferably 0.01 N to 20 N, and more preferably 0.05 N to 10 N.

In principle, the patch case is disposable in the present invention.

However, once used, they can be reused after being cleaned.

When attaching the patch case to the applicator, the patch case may be inserted from the side as in Patent Document 9, but may also be attached to the front surface of the applicator.

Attaching the patch case to the front surface of the applicator prevents the applicator from contacting the subject's skin during microneedle patch application.

When the applicator is not in contact with the skin, there is no risk of cutaneous infection, when the applicator is administered successively to a large number of people and the patch cases are replaced person to person.

In this statement, the side of the applicator close to the skin in use is defined as the front of the applicator.

The patch case may be attached to the front of the applicator by screwing, method, adhesive, etc. The patch case requires to be easily attached to the applicator and to be easily removed.

As the adhesive in the adhesive tape of the microneedle patch, an acrylic or rubber adhesive is used. The thickness of the pressure-sensitive adhesive is 20 to 200 μm.

Advantage of the Invention

When the microneedle patch is adhered to the patch case, the thermal fusion bonding method is superior to the method using the adhesive as the bonding method because the film can be more easily adhered and peeled off as compared with the adhesive method.

Attaching the microneedle patch to the patch case and attaching it to the bottom of the edge of the patch case is easier to peel off than attaching it to the top, making the penetration smoother and better.

When the patch case is attached to the front surface of the applicator, the applicator does not contact the skin of the recipient and health can be maintained even in the case of continuous use for many subjects.

The patch case of the present invention is not only capable of storing, transporting, and holding the microneedle patch safely and hygienically, but is also attached to the applicator together with the case immediately for use.

So that it does not require complicated attachment and is convenient for the user.

DETAILED DESCRIPTION OF THE INVENTION

Embodiments of the present invention will be described below based on examples.

However, the present invention is not limited to the content of the examples.

Example 1

In this example, the patch case of the present invention was used with applicator of Patent Document 9.

When used with other applicators, modifications in shape and dimensions are of course necessary.

Such modifications may be made within the scope of the present invention.

In the applicator of Patent Document 9, a patch case to which a microneedle patch is mounted is inserted from a side surface of the applicator.

The patch case of the present embodiment was fabricated by injection molding using polypropylene (Novatec MA3H, Nippon Polypropylene Industries, Ltd.) as the material of the two embodiments.

Figure 1:
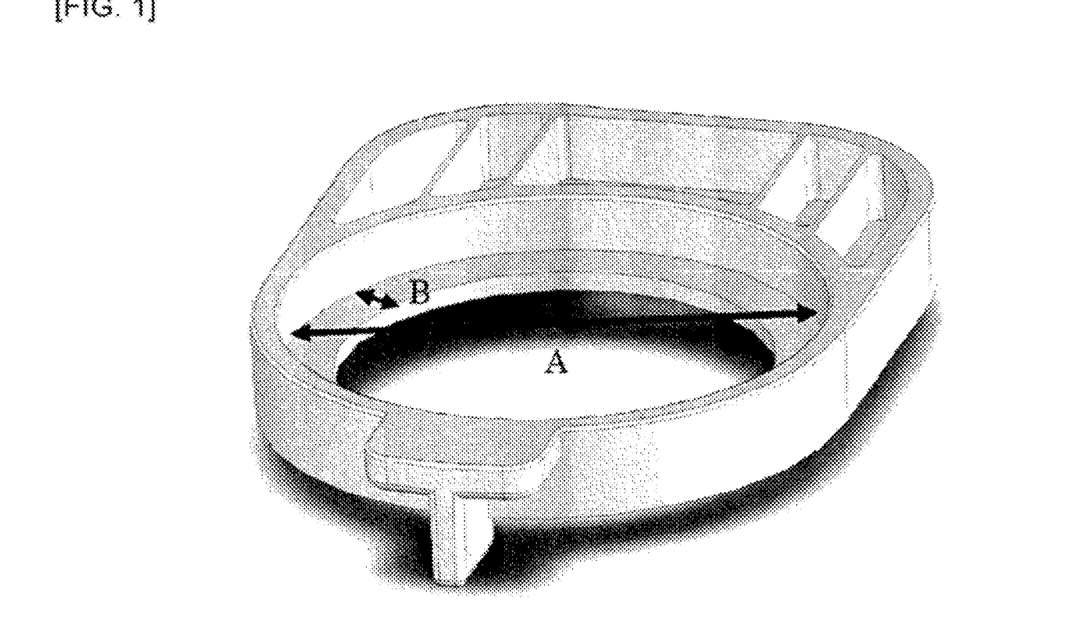
FIG. 1 is a perspective view of an embodiment of a patch case of Example 1.
Figure 2:
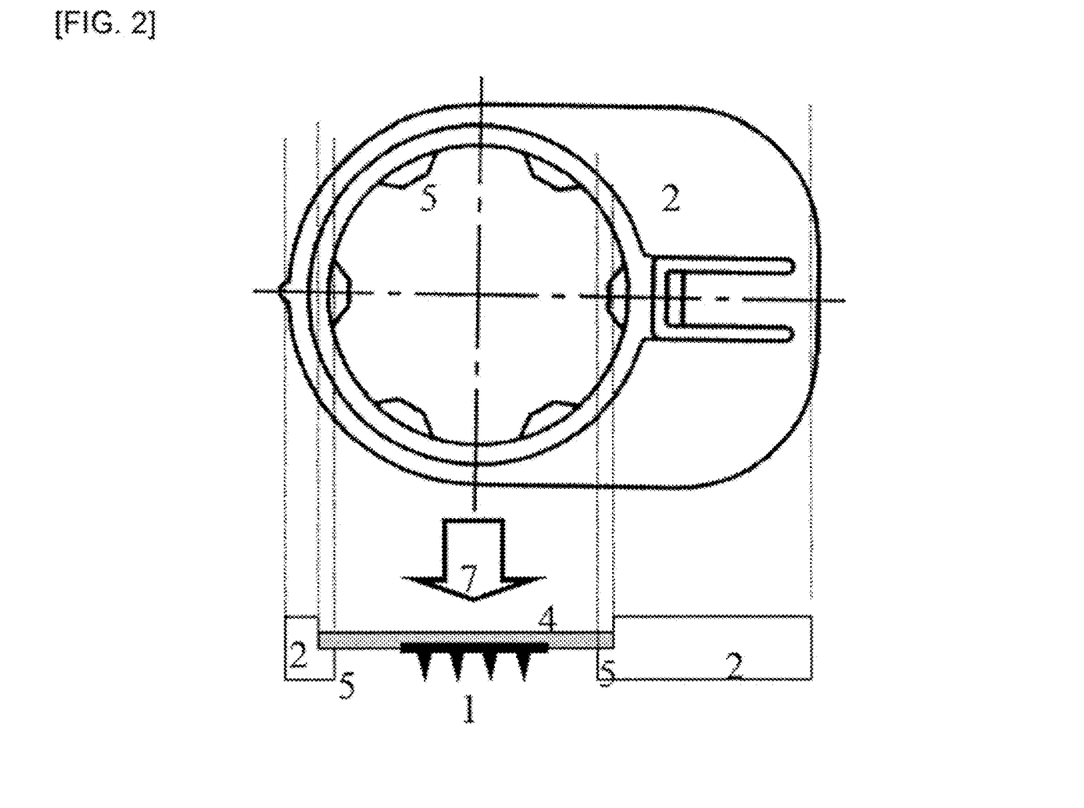
FIG. 2 is a plan view and a cross-sectional view of another embodiment of the patch case of Example 1.

One perspective view thereof is shown in FIG. 1, and another plan view and a center cross-sectional view thereof are shown in FIG. 2.

Both are of approximately the same size, with a circular hole of the same size in the central (the inner diameter of which is shown as A in FIG. 1) and a slightly smaller inner diameter edge at the bottom of the hole (shown as B in FIG. 1).

One difference between the two is that the edges of FIG. 1 are all connected, while the edges of FIG. 2 are flared.

The diameter (A) of the central hole was 29 mm in both cases, and the width (B) of the edge was 3 mm in both cases.

In the patch case of FIG. 1, the microneedle patch was thermally fused under the edge, while in the patch case of FIG. 2, the microneedle patch was adhered over the edge using an adhesive applied to the adhesive tape of the microneedle patch.

That is. the two prototype patch cases differ in the installation method and the bonding method, and the effects of these differences were compared in this example.

Reflecting this difference, in FIG. 1, a comparison was made between a case in which the support film was fused to the patch case and then the microneedle array was adhered and a case in which the microneedle array was adhered and held to the adhesive surface and the adhesive surface of the support film was adhered to the upper surface of the patch case.

In FIG. 2, the microneedle array was bonded to the support film and then to the patch case.

Incidentally, it is also possible to attach from below by a fusion bonding method using the one shown in FIG. 2.

The material of the microneedle array used was hyaluronic acid, and about 260 needles with a height of 0.8 mm were standing on a circular substrate with a diameter of 10 mm.

The support film had a circular diameter of 28 mm, and the material was a polypropylene/PET laminate film (Panac Co., Ltd.), and an acrylic adhesive (HiPAS, manufactured by Cosmed Pharmaceutical Co., Ltd.) was applied to a thickness of 50 μm on the PET, which is the front surface (lower side as viewed from the patch case).

When the patch case of FIG. 1 was used, the microneedle patch was placed under the edge of the central hole in the patch case, the polypropylene side of the support film was placed under the edge, and spot welding was performed at six directions equiangularly and equidistantly spaced from below the edge to secure the support film to the patch case.

Figure 6:
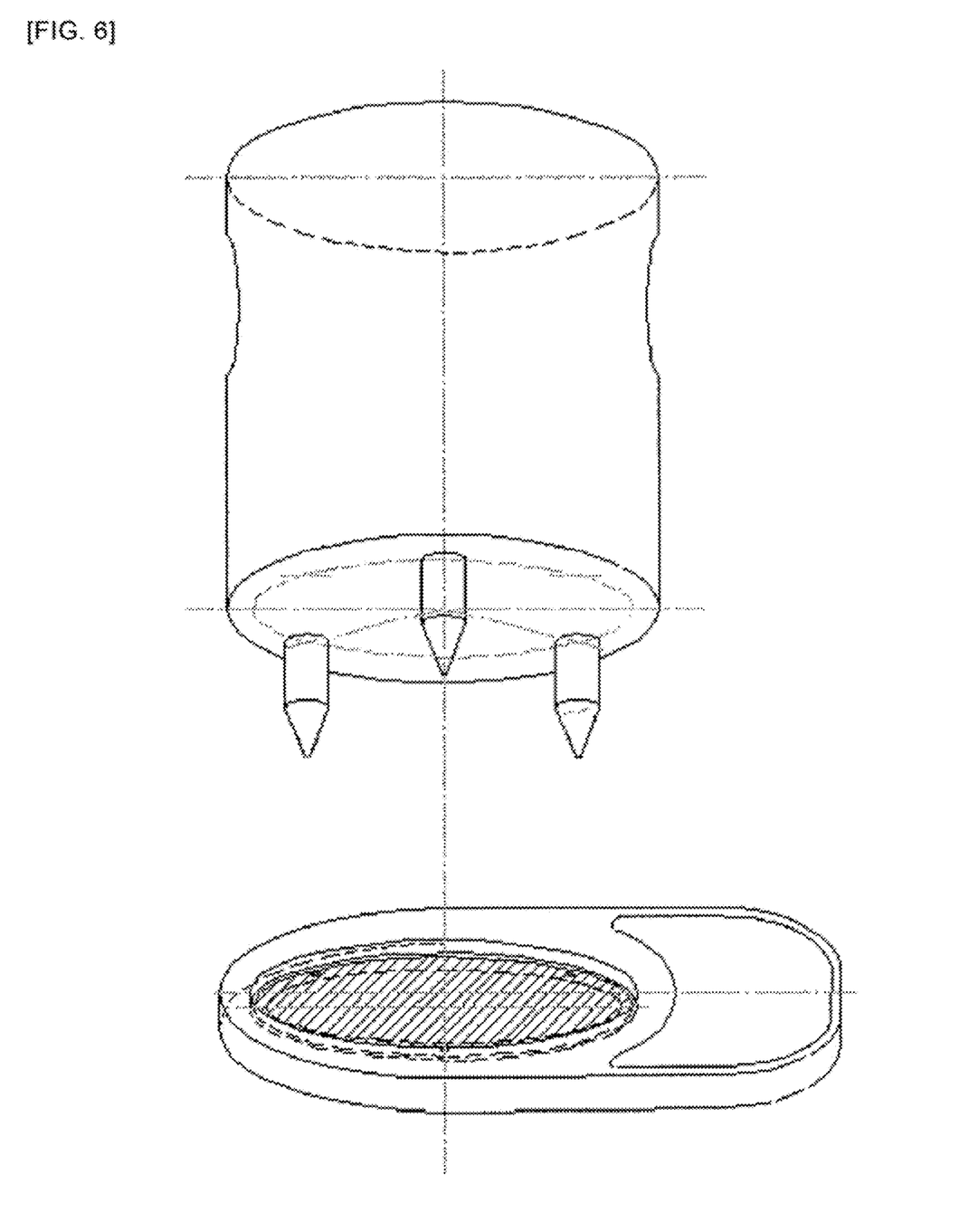
FIG. 6 is an example of an device for three-point thermal fusion bonding of a patch case and a support film.

This is performed by an device as shown in FIG. 6 for thermally fusing the patch case and the support film.

The upper metal portion is heated to press the pointed three points against the adhesive surface of the support film to fuse the support film and the patch case.

This figure is a schematic view of three-point fusion.

A more detailed description will be given with reference to FIG. 3.

FIG. 3 shows across-sectional view of the body 2 of the patch case and its edges 5 and the support films 3, 4 of the microneedle array 1 attached to the edges.

The support film in this case is a laminate of an adhesive tape 4 and a thermoplastic film 3.

The microneedle patch is placed on the edge 5 of a patch case made of thermoplastics.

The six pointed metal fusing heads 6 are heated above the melting point of the thermoplastic resin and pressed from above the adhesive tape 4 to fuse the support film and the patch case.

As a metal fusing head, a 6 mm iron round rod whose tip end was sharpened to a tip angle of about 15 degrees and whose tip end was processed into a spherical surface having a radius of about 0.5 mm was used.

Each fusing head is heated uniformly.

Light fusing is desirable to the range that the support film does not separate from the case during storage.

Although the microneedle array is adhered to the support film before fusing in the drawing, the microneedle array may be adhered and held at the central of the support film after the support film and the patch case are thermally fused.

In this example, the temperature of the tip of the fusing head was about 190° C.

A stopper was provided so that the heated tip of the fusing head was stopped when it was pushed about 0.5 mm deep from the surface of the support film, and the stopper was set so as not to be pushed further.

The fuser head was held in contact for about 0.5 seconds after striking the stopper, and the fuser head was immediately released.

When the support film was fused first, the microneedle array was adhesively held in the center portion of the support film after the fusing operation.

In addition, the whole was packaged in aluminum bags to ensure safety during storage and transportation.

In order to optimize the fusing state, it is desirable to adjust three conditions: the temperature of the fusing metal rod, the pushing amount of the fusing metal rod, and the holding time of the fusing metal rod at the pushing position.

It is also effective to lower the adhesiveness of the welding metal rod to the pressure-sensitive adhesive by applying a fluorine resin or the like.

It is necessary to satisfy the condition that the fusing is ensured, the support film is not detached from the patch case during storage, and all the fused portions are reliably detached uniformly during use.

At the application, the fusion between the support film and the patch case was peeled off by impact (the impact direction is indicated by the arrow 7 in FIGS. 2 and 3) from the back surface direction of the microneedle patch, and the microneedle allay was administered to the skin of the subject.

The prepared patch case/microneedle patch was attached to an applicator of Patent Document 9 and administered to the skin.

One time after dose, the microneedle allays were collected and observations were made under a microscope to determine whether all microneedles were inserted vertically into the skin and evenly dissolved.

The performance of two prototype patch cases was compared.

The results are given in Table 1.

Ten administrations were made to determine the number of microneedles which were nearly straight and dissolved to the root (appropriate case) and the number microneedles which were bent and not sufficiently dissolved (inappropriate case).

TABLE 1

| Patch case | Bonding method of microneedle patch case | Evaluation result of ten administrations | |
|---|---|---|---|
| | | Appropriate case | Inappropriate case |
| In FIG. 1 | Thermally fused to the under surface of the edge | 10 | 0 |
| | Adhered to the upper surface of the edge | 2 | 8 |
| In FIG. 2 | Thermally fused to the under surface of the edge | 10 | 0 |
| | Adhered to the upper surface of the edge | 7 | 3 |

The following conclusions can be drawn from the results in Table 1.

(1) The removing of microneedle patch from the patch case can be much smoother by the heat fusion method than by the adhesive method.

(2) The microneedle patch can be smoothly removed by mounting it below the edge of the patch case.

Example 2

Mounting the patch case/microneedle patch on the front most surface of the applicator has the advantage that the applicator does not contact the skin during dose.

Figure 4:
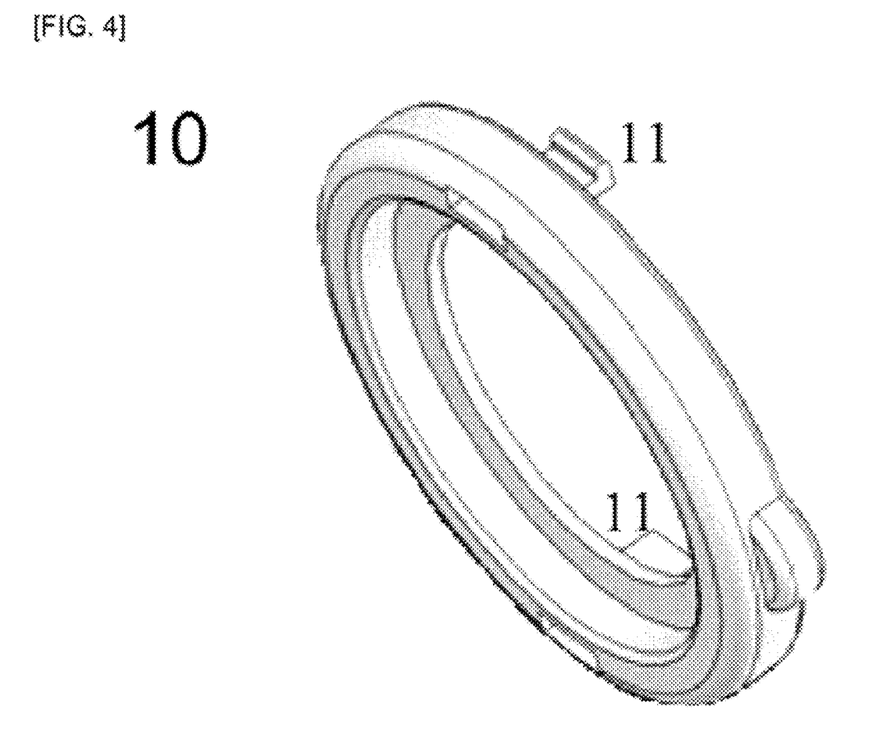
FIG. 4 is a perspective view of a patch case of Example 2.

In order to mount the patch case on the foremost surface of the applicator, a prototype patch case 10 as shown in FIG. 4 was manufactured.

The patch case 10 includes two clasps 11 for mounting to an applicator.

Figure 5:
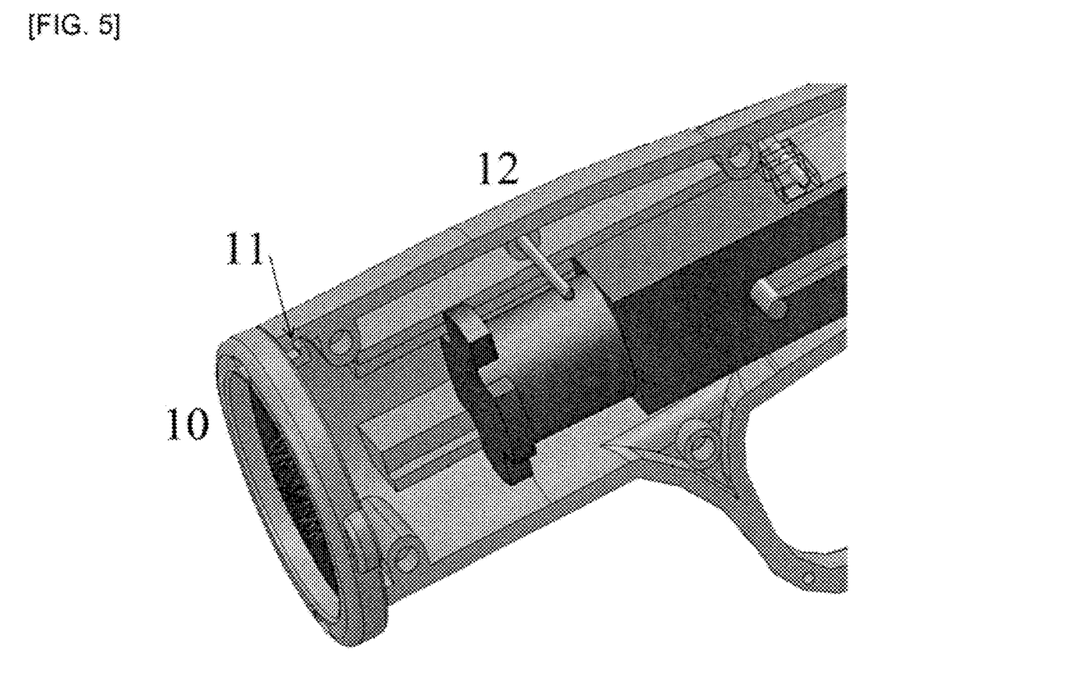
FIG. 5 is a photograph of the patch case of Example 2 attached to an applicator.

FIG. 5 shows a patch case 10 to which a microneedle patch is attached by thermal fusion, and is fitted and attached to an applicator 12 by using a clasp.

The patch case may be disposable, and the microneedle patch may be shipped with the patch case preloaded.

Since the patch case is attached to the front of the applicator, when the microneedle patch is administered to the subject, the patch case contacts the skin of the subject, but the applicator does not contact the skin of the subject.

When successively dose microneedle patches to multiple recipients, the same applicator can be used successively without risk of cutaneous infection by replacing the disposable patch case to which the microneedle patches are attached.

Example 3-6, Comparative Example 1-2

Patch cases with support films having different break strengths were produced by varying the heat-fusing conditions.

A polyethylene (50 μm thick)/PET (20 mm thick) laminated film (Panac Corporation) was used as the support film.

The support film was a PET film having was circular with a diameter of 28 mm, and an acrylic adhesive (HiPAS, manufactured by Cosmedy Pharmaceutical Co., Ltd.) was applied to a thickness of 50 μm on the PET film having a diameter of 28 mm and a front surface (downward side as viewed from the patch case).

The patch case was injection molded in the shape of FIG. 4 and the material was high density polyethylene (Novatech HD, Nippon Polyethylene Co., Ltd.).

The edge of the patch case, 5 in FIG. 3, had an area sufficient to heat bond the support film, and the inner diameter of the patch case was 2.3 cm.

The support film and the patch case were fused together in the same manner as in Example 1.

The temperature of the tip of the fusing head was about 190° C.

The heated fuser head tip was pressed and fused about 0.2 mm to 0.5 mm from the surface of the support film.

The fuser head was held in contact for 0.3 to 1 second and immediately released.

The degree of fusing was varied by varying the depth of indentation and the contact time.

The break strength of 5 samples of the fused product produced under the same conditions was measured, and the maximum value and the minimum value thereof were defined as "the fracture strength under the present condition".

The break strength of the thermal fusion was quantified by compressing the fusion surface from above of a patch case with a support film having a structure shown in FIG. 3 using a 1 cm diameter cylindrical rod using a tensile tester.

The study was carried out at 40-60% relative humidity at room temperature.

As the tensile study, a small tabletop tester EZ Test EZSX manufactured by Shimadzu Seisakusho Co., Ltd. was used.

The compression speed was 10 mm/min.

Details of the dosing study were as follows.

The applicator as shown in FIG. 5 was fitted with a patch case with a microneedle patch having a microneedle array centrally adhered thereto.

The microneedle patch was set on the applicator and applied into the abdominal of shaved male Wistar rats and microneedle arrays were immediately collected.

The skin at the administration site was wetted with an aqueous solution of 1% Gentian Violet 8 (Wako Pure Chemical Industries, Ltd.), and the skin condition after wiping with gauze was observed to evaluate the administration result.

The material of the microneedle array used was polyglycolic acid (Kureha Corporation), and about 800 needles with a height of 0.6 mm were erected on a circular substrate with a diameter of 10 mm.

All samples were stored and tested for transport stability prior to dosing.

In this test, peeling of the fused portion was observed 10 times by repeating natural dropping of the integrated microneedle array/support film/case from a height of 1 m to the floor. The results are shown in Table 2.

TABLE 2

| Example, Comparative Example | Heat-fusing pattern | Fusing condition (the depth of indentation/ the contact time) (mm/second)) | The fracture strength under the present condition (N) | Transport stability test | The administration result |
|---|---|---|---|---|---|
| Example 3 | 6-point fusion (perfect circle) | 0.3/0.3 | 0.5~1.0 | No problem | Appropriate |
| Example 3 | 6-point fusion (perfect circle) | 0.3/0.3 | Same as above | No problem | Appropriate |
| Example 4 | 6-point fusion (perfect circle) | 0.5/0.5 | 3.0~5.0 | No problem | Appropriate |
| Example 4 | 6-point fusion (perfect circle) | 0.5/0.5 | Same as above | No problem | Appropriate |
| Example 5 | dash line fusion | 0.5/0.5 | 7.0~10.0 | No problem | Appropriate |
| Example 5 | dash line fusion | 0.5/0.5 | Same as above | No problem | Appropriate |
| Example 6 | dash line fusion | 0.5/1.0 | 10.0~20.0 | No problem | Appropriate |
| Example 6 | dash line fusion | 0.5/1.0 | Same as above | No problem | Appropriate |
| Example 7 | full point fusion | 0.2/1.0 | 0.01~0.06 | No problem | Appropriate |
| Example 7 | full point fusion | 0.2/1.0 | Same as above | No problem | Appropriate |
| Comparative Example 1 | solid line fusion | 0.5/1.0 | 30~40 | No problem | Inappropriate |
| Comparative Example 1 | solid line fusion | 0.5/1.0 | Same as above | No problem | Inappropriate |
| Comparative Example 2 | 3-point fusion (perfect circle) | 0.3/0.2 | 0.005~0.009 | Partial peeling of the fused portion | — |
| Comparative Example 2 | 3-point fusion (perfect circle) | 0.3/0.2 | Same as above | Partial peeling of the fused portion | — |

Appropriate: It was observed that due to depth of blue color of the skin stained all the microneedles were inserted.
Inappropriate: It was observed that due to depth of blue color of the stained skin a part of microneedles cannot be inserted. Further, a part of the substrate sheet remained without peeled.

DESCRIPTION OF THE SYMBOLS

1 Microneedle array
2 Patch case
3 Support film of microneedle patch
4 Adhesive-tape of microneedle patch
5 Edge of the patch case 6 Fuser heads of metal
7 Impact direction of the applicator
10 Patch Case for Applicator Front Mounting
11 Clamp
12 Applicator

The invention claimed is:

1. A patch case comprising a thermoplastic polymer material, holding a microneedle patch comprising a support film which is heat-sealable to the thermoplastic polymer material, wherein
 a fusion surface of the microneedle patch is attached to the underside of an edge of the patch case by thermal fusion, and
 a break strength of a thermally fused portion is 0.01 to 20 N per unit, the unit being the area of a circle having a diameter of 1 cm, the break strength being quantified by compressing the fusion surface from above using a cylindrical rod having a diameter equal to a diameter of the fusion surface.

2. The patch case of claim 1, wherein the thermoplastic polymer material and a micro-sealable material of the support film are both polyolefins.

3. The patch case holding the microneedle patch as claimed in claim 1, wherein the thermoplastic polymer material and a heat-sealable material of the support film are the same thermoplastic polymers.

4. The patch case holding the microneedle patch according to claim 1, wherein a thermal fusion pattern is three or more points of multiple-point fusion, dashed-line fusion, solid-line fusion, or full-feature fusion.

5. The patch case holding the microneedle patch as claimed in claim 1, further comprising a clasp or a screw for attaching the patch case to a front face of an applicator.

6. A method of using the patch case as claimed in claim 1, comprising
 holding the microneedle patch in the patch case,
 heat fusing the support film of an adhesive tape to the thermoplastic polymer material, said support film being made of a thermoplastic polymer holding thereon a material capable of being heat-fused with the thermoplastic polymer material, and
 attaching the patch case to a front surface of an applicator.

* * * * *